US012539196B2

(12) United States Patent
Madan

(10) Patent No.: US 12,539,196 B2
(45) Date of Patent: Feb. 3, 2026

(54) BIOPSY DEPLOYER WITH AUTOMATIC PLUNGER RETRACTION

(71) Applicant: Devicor Medical Products, Inc., Cincinnati, OH (US)

(72) Inventor: Ashvani Madan, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 231 days.

(21) Appl. No.: 18/196,670

(22) Filed: May 12, 2023

(65) Prior Publication Data

US 2023/0277275 A1 Sep. 7, 2023

Related U.S. Application Data

(63) Continuation of application No. PCT/US2021/061386, filed on Dec. 1, 2021.

(60) Provisional application No. 63/120,474, filed on Dec. 2, 2020.

(51) Int. Cl.
*A61B 90/00* (2016.01)

(52) U.S. Cl.
CPC ...... *A61B 90/39* (2016.02); *A61B 2090/3908* (2016.02); *A61B 2090/3987* (2016.02)

(58) Field of Classification Search
None
See application file for complete search history.

(56) References Cited

U.S. PATENT DOCUMENTS

| | | | | |
|---|---|---|---|---|
| 6,083,524 | A | 7/2000 | Sawhney et al. | |
| 6,162,241 | A | 12/2000 | Coury et al. | |
| 6,270,464 | B1 | 8/2001 | Fulton, II et al. | |
| 6,356,782 | B1 | 3/2002 | Sirimanne et al. | |
| 6,605,294 | B2 | 8/2003 | Sawhney | |
| 8,600,481 | B2 | 12/2013 | Sirimanne et al. | |
| 8,939,910 | B2 | 1/2015 | Fisher | |
| 2012/0220954 | A1 * | 8/2012 | Cowe | A61M 5/2033 604/228 |

FOREIGN PATENT DOCUMENTS

| | | | |
|---|---|---|---|
| DE | 102015003601 | A1 | 9/2016 |
| EP | 3000498 | A2 | 3/2016 |
| WO | 2017/040064 | A1 | 3/2017 |

OTHER PUBLICATIONS

International Search Report and Written Opinion dated Jul. 3, 2022 for Application No. PCT/US2021/061386, 13 pages.

* cited by examiner

*Primary Examiner* — Amelie R Davis
(74) *Attorney, Agent, or Firm* — FBT Gibbons LLP

(57) ABSTRACT

A marker delivery device includes a handle, an elongate cannula, a push rod assembly, and a plunger. The handle includes a first bore disposed within a portion of the handle. The elongate cannula extends distally from the handle along a longitudinal axis. The push rod assembly includes a mating feature. The push rod assembly is disposed within the first bore and extends distally through the cannula. The plunger is disposed within the first bore proximally of the push rod assembly and includes an engagement feature. The engagement feature is removably coupled to the mating feature. The engagement feature is configured to de-couple from the mating feature when the plunger translates the push rod assembly distally.

20 Claims, 11 Drawing Sheets

BIOPSY DEPLOYER WITH AUTOMATIC PLUNGER RETRACTION

PRIORITY

This application is a continuation of International Application Number PCT/US2021/061386, entitled "A Marker Delivery Device Configured to Decoupled Plunger and Push Rod," filed on Dec. 1, 2021, which claims priority to U.S. Provisional Application Ser. No. 63/120,474, entitled "Biopsy Deployer with Automatic Plunger Retraction," filed on Dec. 2, 2020, the disclosures of which are incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of an image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

Markers are described in the following US Patents: U.S. Pat. No. 6,083,524, "Polymerizable Biodegradable Polymers Including Carbonate or Dioxanone Linkages," issued Jul. 4, 2000; U.S. Pat. No. 6,162,241, "Hemostatic Tissue Sealants," issued Dec. 4, 2000; U.S. Pat. No. 6,270,464, "Biopsy Localization Method and Device," issued Aug. 7, 2001; U.S. Pat. No. 6,356,782, "Subcutaneous Cavity Marking Device and Method," issued Mar. 12, 2002; U.S. Pat. No. 6,605,294, "Methods of Using In Situ Hydration of Hydrogel Articles for Sealing or Augmentation of Tissue or Vessels," issued Aug. 12, 2003; U.S. Pat. No. 8,600,481, "Subcutaneous Cavity Marking Device," issued Dec. 3, 2013 and U.S. Pat. No. 8,939,910, "Method for Enhancing Ultrasound Visibility of Hyperechoic Materials", issued Jan. 27, 2015. All of these US Patents are incorporated by reference, in their entirety.

In some contexts, a marker deployer requires an operator to press a plunger or plunger to translate a marker through a cannula using a push rod. Once the plunger is pressed, the push rod may protrude from a lateral aperture of a needle. After the marker is deployed, but before removing the deployer, the operator must release the plunger. The step of releasing the plunger, to some operators, is not always intuitive. As a result, a sharp edge of the lateral aperture or other surfaces associated with the biopsy device can shear the tip of the push rod leaving foreign objects in the body.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings, some components or portions of components are shown in phantom as depicted by broken lines.

Figure 1C:
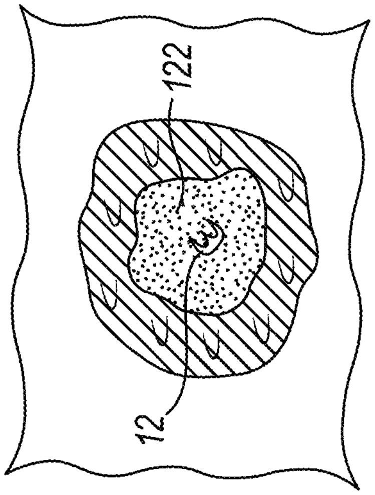
FIGS. 1A, 1B, and 1C show exemplary aspects of placement of a biopsy site marker, in accordance with aspects of the present disclosure.

The drawings are not intended to be limiting in any way, and it is contemplated that various embodiments of the invention may be carried out in a variety of other ways, including those not necessarily depicted in the drawings. The accompanying drawings incorporated in, and forming a part of the specification, illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

I. EXEMPLARY MARKER

Figure 1B:
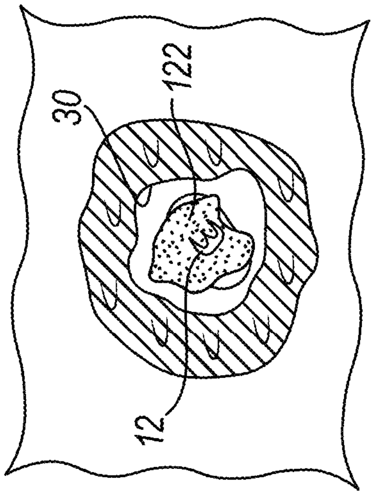
Figure 1A:
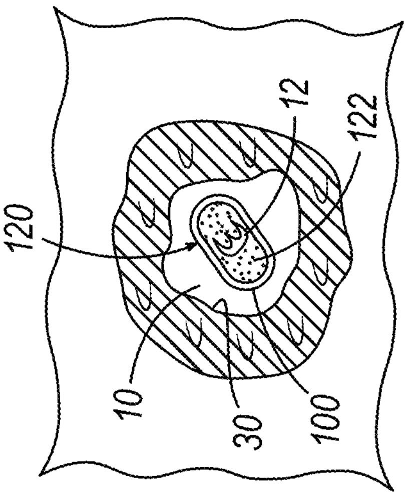

Aspects presented herein relate to devices and procedures for manufacturing a marker for percutaneously marking a biopsy cavity (10) having surrounding tissue (30), as shown in FIGS. 1A-1C. For instance, as seen in FIG. 1A, a marker (100) may be initially placed in the biopsy cavity (10) to facilitate relocation of the biopsy site. Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some examples, carrier (120) can include a plurality of microbubbles to enhance visualization of carrier (120) under ultrasound. As will be described in greater detail below, marker material (122) is generally bioabsorbable such that marker material (122) may be generally absorbed into the patient's tissue over time. In the present example, marker material (122) comprises a hydrogel that is initially in a dehydrated state. Although a hydrogel is used in the present example, it should be understood that in other examples marker material (122) may comprise other known bioabsorbable materials.

In the present example, marker (100) further includes marker element (12) that is generally not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without marker element (12). In still other examples, marker (100) may be formed with only marker element (12) such that carrier (120) is omitted and marker element (12) is in a "bare" form. In other words, in some examples, marker (100) is formed of only carrier (120) as a bare clip.

Marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, marker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured, and the natural mechanical parameters of the tissue are substantially restored to those of the pre-damaged condition.

Marker (100) may be inserted into the body either surgically via an opening in the body cavity tissue (30), or through a minimally invasive procedure using such devices as a catheter, introducer or similar type insertion device. Marker (100) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) of the present example is large enough to be readily visible to a clinician under x-ray or ultrasonic viewing, for example; yet small enough to be able to be percutaneously deployed into the biopsy cavity and to not cause any difficulties with the patient. Although examples are described in connection with treatment and diagnosis of breast tissue, aspects presented herein may be used for markers in any internal tissue, e.g., in breast tissue, lung tissue, prostate tissue, lymph gland tissue, etc.

The hydration of the marker material (122) of carrier (120) by the natural moisture of the tissue surrounding it causes expansion of the polymer and thus minimizes the risk of migration. The growing hydrogel-based marker material (122) centers marker (100) in the biopsy cavity as it grows. As the hydrogel expands, naturally present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of the permanent marker (12) within the hydrogel hydrated marker material (122) because the permanent marker (12) is outlined as a specular reflector within a hypoechoic hydrated marker having a water-like nonreflective substrate.

II. EXEMPLARY MARKER DELIVERY DEVICE

Figure 2:
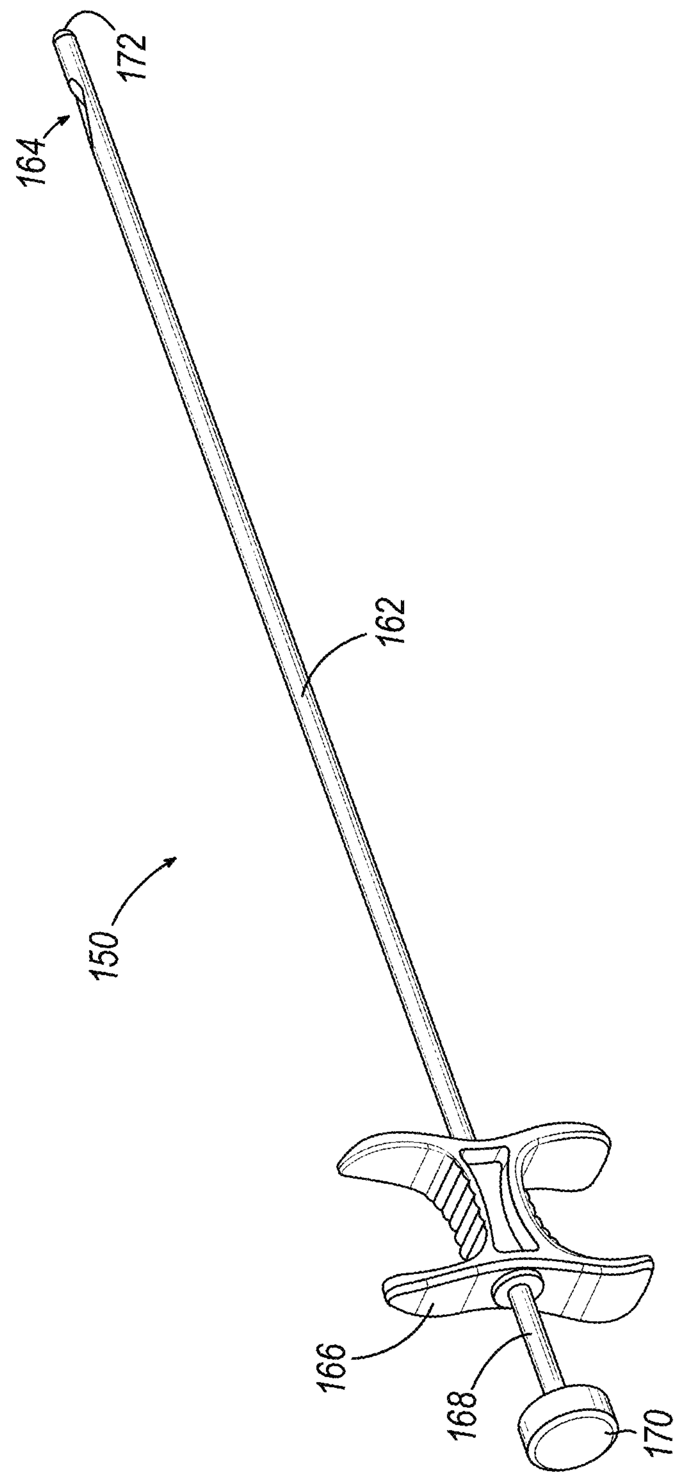
FIG. 2 depicts a perspective view of an exemplary marker delivery device.

In some examples it may be desirable to deploy marker (100) described above within the body cavity tissue (30) using certain marker delivery devices. For instance, FIG. 2 shows an exemplary marker delivery device (150) which includes an elongate outer cannula (162) having a marker exit, such as side opening (164) formed adjacent to, but spaced proximally from, the distal end of the cannula (162).

A grip (166) can be provided at the proximal end of cannula (162). A push rod (168) can be provided, with push rod (168) extending coaxially in cannula (162) such that push rod (168) is configured to translate within cannula (162) to displace one or more markers through side opening (164). Rod (168) may have sufficient rigidity in compression to push marker from an internal lumen (165) of cannula (162) out through opening (164) yet be relatively flexible in bending. A plunger (170) is coupled at the proximal end of rod (168) for forcing rod (168) distally in cannula (162) to deploy marker out of cannula (162).

An operator may grasp grip (166) with two fingers and may push on plunger (170) using the thumb on the same hand, so that marker delivery device (150) is operated by an operator's single hand. A spring (not shown) or another feature may be provided about rod (168) to bias rod (168) proximally relative to grip (166) and cannula (162).

Figure 3:
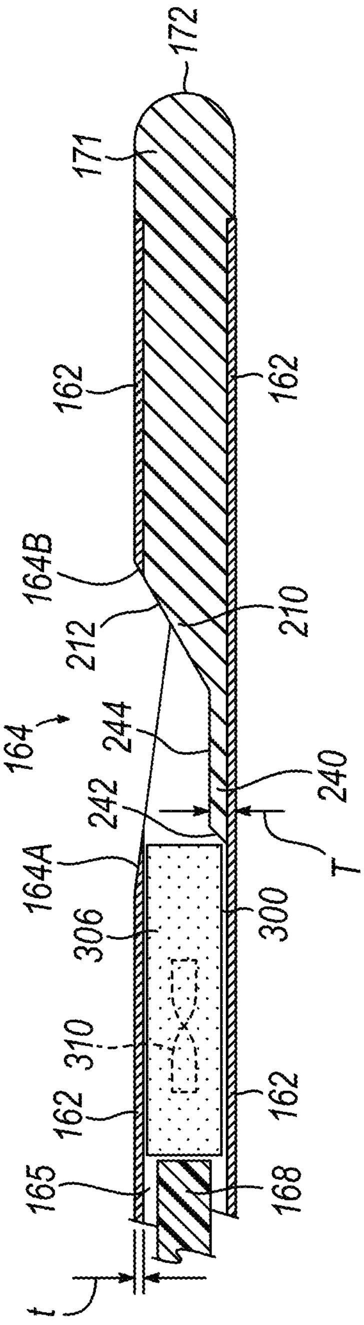
FIG. 3 depicts a side cross-sectional view of the marker delivery device of FIG. 2.

FIG. 3 shows a cross-sectional view of a distal portion of the marker delivery device (160). As can be seen, a biopsy marker (300) similar to marker (100) described above is disposed within internal lumen (165) of cannula (162). In the present example, marker (300) comprises a biodegradable or otherwise resorbable marker material (306), such as a generally cylindrically shaped body of collagen, hydrogel, etc., and a metallic, generally radiopaque permanent marker or marker element (310) (shown in phantom) disposed within or otherwise carried by marker material (306).

Cannula (162) may be formed of any suitable metallic or non-metallic material. In some versions, cannula (162) is formed of a thin walled hollow tube formed of a suitable medical grade plastic or polymer. One suitable material is a thermoplastic elastomer, such as Polyether Block Amide (PEBA), such as is known under the tradename PEBAX®. Cannula (162) may be formed of PEBAX® and may be substantially transparent to visible light and X-ray.

Side opening (164) may be formed by cutting away a portion of the wall of cannula (162). Side opening (164) communicates with an internal lumen (165) of cannula (162). Side opening (164) may extend axially (in a direction parallel to the axis of lumen (165)) from a proximal opening end (164A) to a distal opening end (164B) (see FIG. 3).

In the present example, distal tip (22) extends from the distal end of cannula (162) (see FIG. 2). The distal end of cannula (162) is closed by a unitary endpiece (21) (see FIG. 4), with a portion of endpiece (21) extending into internal lumen (165) of cannula (162). Endpiece (21) may be a molded or cast component. As shown in FIG. 3, endpiece (21) comprises a tip (172), a ramp (210) having a ramp surface (212), and a marker engaging element (240). Ramp surface (212) aids in directing marker (300) from internal lumen (165) through side opening (164). Marker engaging element (240) helps to retain marker (300) in internal lumen (165) until the operator intends to deploy marker (300).

Marker engaging element (240) is disposed within internal lumen (165), and at least a portion of marker engaging element (240) is disposed distally of proximal end (164A) of side opening (164). Marker engaging element (240) extends along a portion of the floor of cannula (162) under side opening (164) such that marker engaging element (240) is positioned to reinforce the portion of cannula (162) in which side opening (164) is formed. For instance, by positioning marker engaging element (240) underneath side opening (164), as shown in FIG. 3, marker engaging element (240) helps to stiffen cannula (162) in the region where wall of cannula (162) is cut to form side opening (164). As shown in FIG. 3, marker engaging element (240) extends from the proximal most portion of ramp surface (212) and does not extend proximally of side opening (164), though in other embodiments, a portion of marker engaging element (240) may extend proximally of opening (164).

As shown in FIG. 3, marker engaging element (240) is in the form of a step having a generally uniform thickness (T) along marker engaging element's (240) axial length, except that marker engaging element (240) has a tapered proximal end (242). Tapered proximal end (242) forms an included angle with the longitudinal axis of lumen (165) (included angle with a horizontal line in FIG. 3) of about 45 degrees, while ramp surface (212) forms an included angle with the longitudinal axis of about 30 degrees. Of course, any number of other suitable angles may be used.

As shown in FIG. 3, an upwardly facing surface (244) (surface facing opening (164)) of marker engaging element (240) extends distally to contact ramp surface (212), so that there is not a space or gap between surface (244) and ramp surface (212). Such an arrangement is advantageous to reduce the possibility that marker (300), upon moving past marker engaging element (240), may become lodged between marker engagement element (240) and ramp (212). In some versions, marker engaging element (240), ramp (210), and/or tip (172) are formed of, or include, a material that is relatively more radiopaque than the wall of cannula (162). For instance, where marker engaging element (240), ramp (210), and tip (172) are formed as an integral endpiece (21) (see FIG. 4), endpiece (21) may include a radiopaque additive, such as barium sulfate. For instance, endpiece (21) may be a component molded of PEBAX®, with about 20 percent by weight barium sulfate added to the molten PEBAX® mold composition. The relatively more radiopaque marker engaging element (240), ramp (210), and tip (172) may be useful in distinguishing the position of those components using radiographic imaging. Also, where ramp (210) and/or step of marker engaging element (240) are positioned in association with opening (164), the addition of a radiopaque material can help identify the position of opening (164), and the position of marker (300) relative to opening (164) before, during, or after deployment of marker (300).

Figure 4:
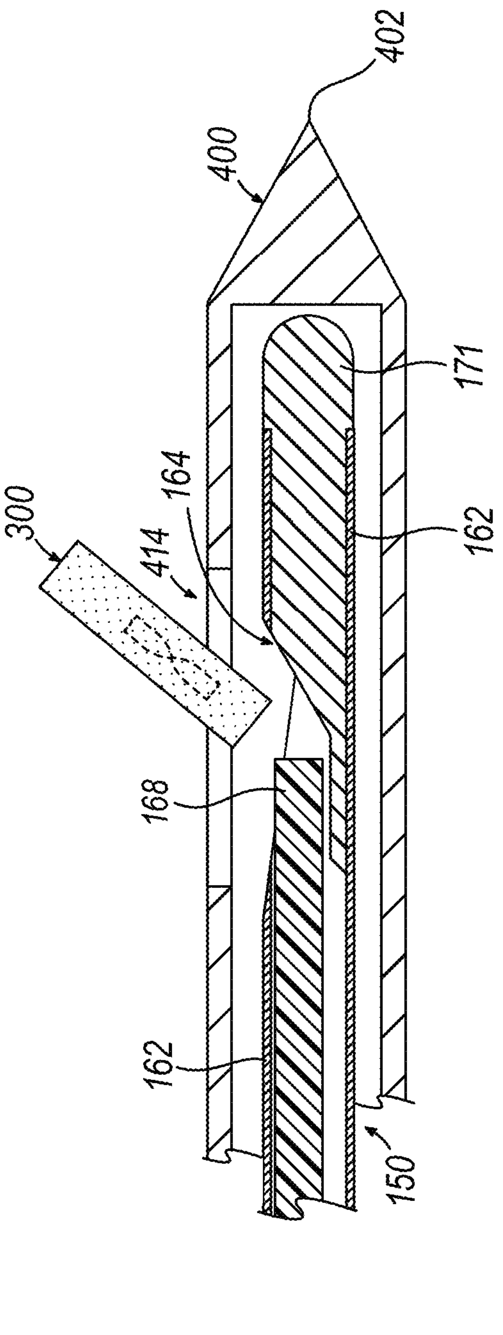
FIG. 4 depicts a cross-sectional view of a marker being deployed from the distal portion of the marker delivery device of FIG. 1, and through a lateral aperture in a biopsy needle to mark a biopsy site.

Referring to FIG. 4, marker delivery device (150) (see FIG. 2) is used to deploy a marker (300) (see FIG. 3) to mark a biopsy location within a patient. In FIG. 4, a cannular biopsy needle (400) is shown having a closed distal end with piercing tip (402) and a lateral tissue receiving side aperture (414) Marker delivery device (150) (see FIG. 2) is introduced to a biopsy site through biopsy needle (400), which may be the same biopsy needle (400) used to collect a tissue sample from the biopsy site. Biopsy needle (400) may be of the type used with single insertion, multiple sample vacuum assisted biopsy devices. Several such biopsy devices are disclosed in the various patents and patent applications that have been referred to and incorporated by reference herein, though other biopsy devices may be used.

FIG. 4 shows the distal end of marker delivery device (150) (see FIG. 2) disposed within needle (400). Biopsy needle (400) may be positioned in tissue, and a biopsy sample may be obtained through lateral aperture (414), thereby providing a biopsy cavity adjacent lateral aperture (414). Then, after the tissue sample has been obtained and transferred proximally through biopsy needle (400), and without removing biopsy needle (400) from the patient's tissue, marker delivery device (150) is inserted into a proximal opening in biopsy needle (400). In FIG. 4, biopsy needle (400) and marker delivery device (150) are positioned such that opening (164) of cannula (162) and lateral aperture (414) of biopsy needle (400) are substantially aligned axially and circumferentially. Then, with marker delivery device (150) and biopsy needle (400) so positioned at the biopsy site, plunger (168) (see FIG. 3) is advanced to deploy marker (300) up ramp surface (212), through opening (164), and then through lateral aperture (414), into the biopsy cavity.

III. EXEMPLARY MARKER DELIVERY DEVICE AUTOMATIC PLUNGER RETRACTION

In some examples, it may be desirable to have a marker delivery device similar to marker delivery device (150) (see FIG. 2), that automatically retracts a plunger after an operator presses a plunger to deploy a marker. In particular, when an operator fully presses the plunger with a finger or a thumb, the plunger distally translates, pushing a marker through a side opening of a needle. When the plunger is distally translated, the plunger tip can protrude from side opening. If the operator inadvertently leaves their finger or thumb on the plunger, the plunger tip may remain protruded from side opening. If the operator removes the marker delivery device from a biopsy needle with plunger pressed, the protruding plunger tip can be severed through engagement against a sharp edge of the biopsy needle or cutter. After the plunger tip is sheared off, a portion of the plunger tip may remain in the patient's body. Thus, in some examples is may be desirable to have a marker delivery device that automatically translates the plunger proximally after marker deployment.

Figure 5:
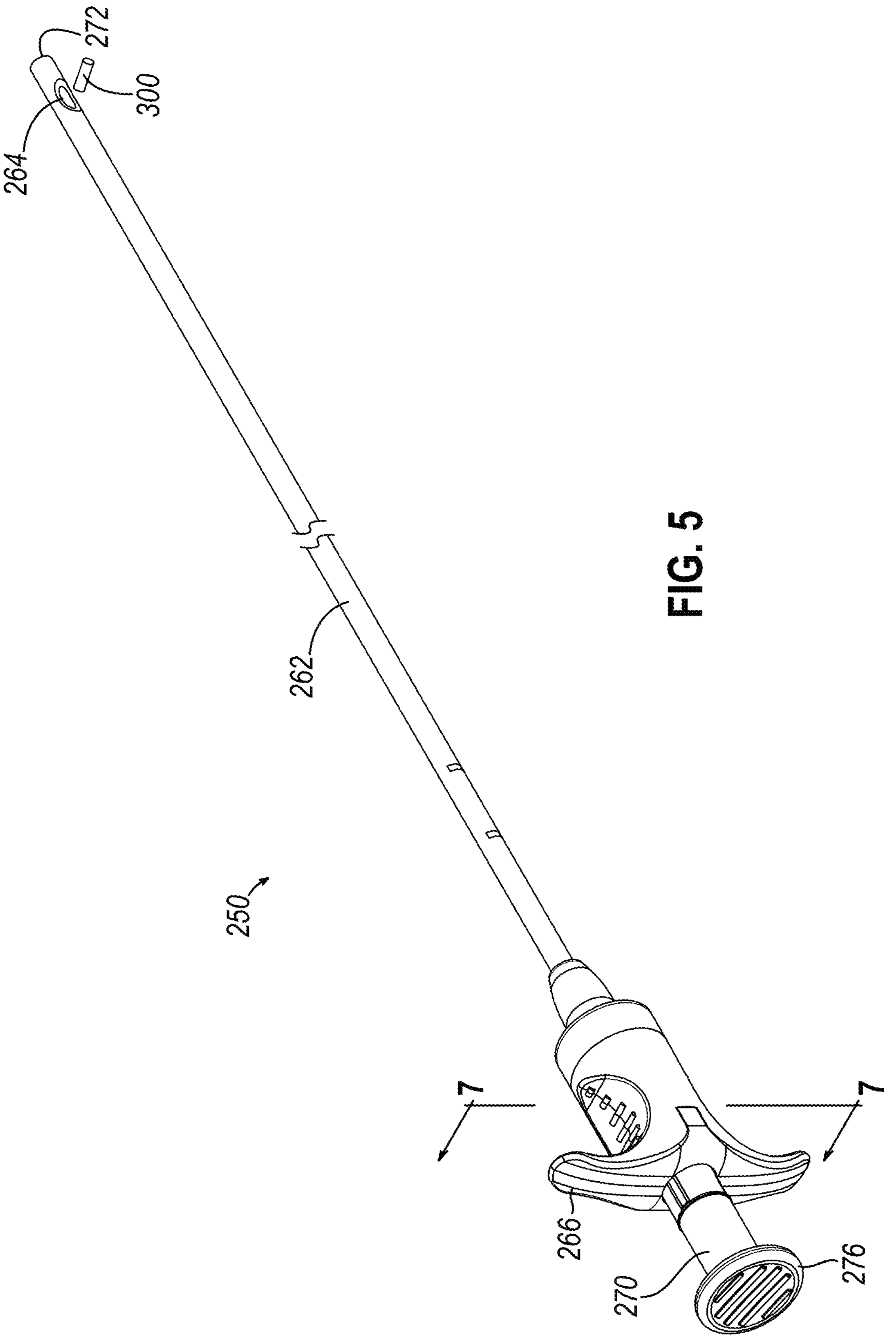
FIG. 5 depicts a perspective view of another exemplary marker delivery device.

FIG. 5 shows an exemplary marker delivery device (250) that is generally configured to deploy a marker (300) through a side opening (264). Marker delivery device (250) is substantially similar to marker delivery device (150) described above except where explicitly noted herein. Like with marker delivery device (150), marker delivery device (250) has an elongate cannula (262), a grip (266), a plunger (270), a push rod assembly (268) (see FIG. 6) and a side opening (264). As with elongated cannula (162) described above, elongated cannula (262) of the present example extends distally from the grip (266). Grip (266) is configured for the operator to hold and manipulate marker delivery device (250). Plunger (270) is configured to translate marker (300) through side opening (264).

Figure 6:
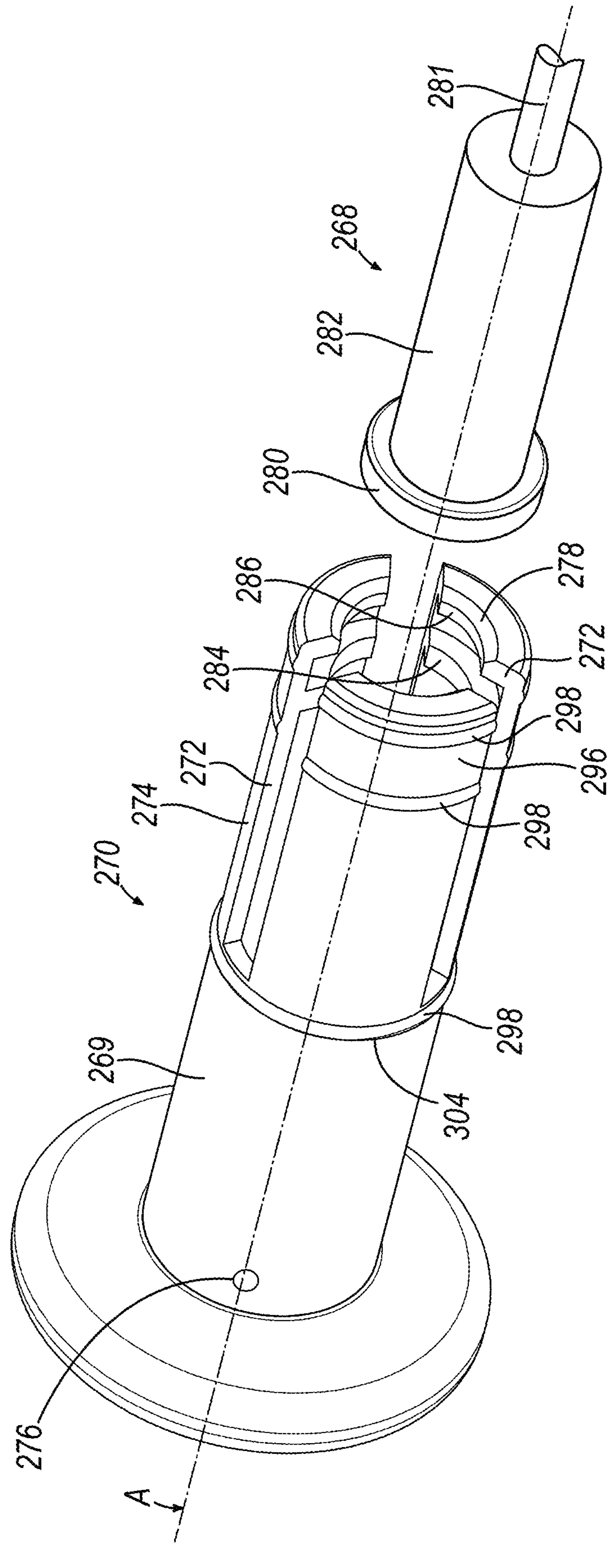
FIG. 6 depicts an enlarged perspective view of a plunger and a proximal end of a push rod assembly.

FIG. 6 shows plunger (270) and push rod assembly (268). However, unlike marker delivery device (150) that has plunger (170) fixed to push rod (168) (see FIG. 2), marker delivery device (250) (see FIG. 5) has plunger (270) removably coupled to push rod assembly (268). Plunger (270) includes one or more arms (274) and a vent (266). As will be described in greater detail below, arms (274) are generally configured to move relative to push rod assembly (268) to permit automatic retraction of push rod assembly (268) relative to plunger (270). Although plunger (270) of the present example includes three arms (274), it should be understood that in other examples, plunger (270) can be configured with any suitable number of arms (274).

Plunger (270) is hollow and includes a vent (266). Vent (266) can be located in the proximal end of plunger (270). Vent (266) can also be located in a proximal portion of plunger sidewall (269). Vent (266) enables egress of air through marker delivery device (250). Atmosphere is in communication with vent (266), such that air can pass through the hollow plunger (270) to elongate cannula (262). The elongated cannula (262) has a hollow around push rod (281). This hollow around push rod (281) allows air to exit the patient's body when marker (300) is deployed through side opening (264) of elongated cannula (262). Arms (274) are configured to transition between a biased state and an unbiased state. Arms (274) are shown in unbiased state. Arms (274) have one or more dogs (296) per arm (270) and one or more exterior bands (298) per arm (270). Dog (296) has a first rib (284) and a second rib (286). Dog (296) is configured to removably couple to at least a portion of push rod assembly (268). First rib (284) is located on a distal interior portion of dog (296) and proximally from second rib (286). Second rib (286) is spaced distally from first rib (284) and located on distal end of dog (296). First and second ribs (284, 286) are spaced apart in order to removably retain a portion of push rod assembly (268) between first and second ribs (284, 286). Second rib (286) has an angular surface (278) located on a distal interior portion of second rib (286). In other embodiments, a single rib (286) may engage two annular rings (280). In further embodiments, any number of ribs (286) may engage any number of annular rings (280).

Exterior bands (298) are longitudinally positioned on an exterior surface of arms (274) and an arm base (304).

Exterior bands (298) are configured to engage a portion of the interior of the handle (266) (see FIG. 5) to provide tactile feedback to the operator.

Plunger (268) includes annular ring (280), a barrel (282), and a push rod (281). Annular ring (280) is proximally located in relation to barrel (282). Annular ring (280) is larger in diameter than barrel (282). Barrel (282) is proximally located in relation to push rod (281). Barrel (282) is larger in diameter than push rod (281). Push rod (281) distally extends through second bore (308) (see FIG. 7) and further extends distally through elongated cannula (262) (see FIG. 8A) to a push rod distal tip (not shown). Push rod distal tip (not shown) is located distal in relation to side opening (264) (see FIG. 5).

Figure 7:
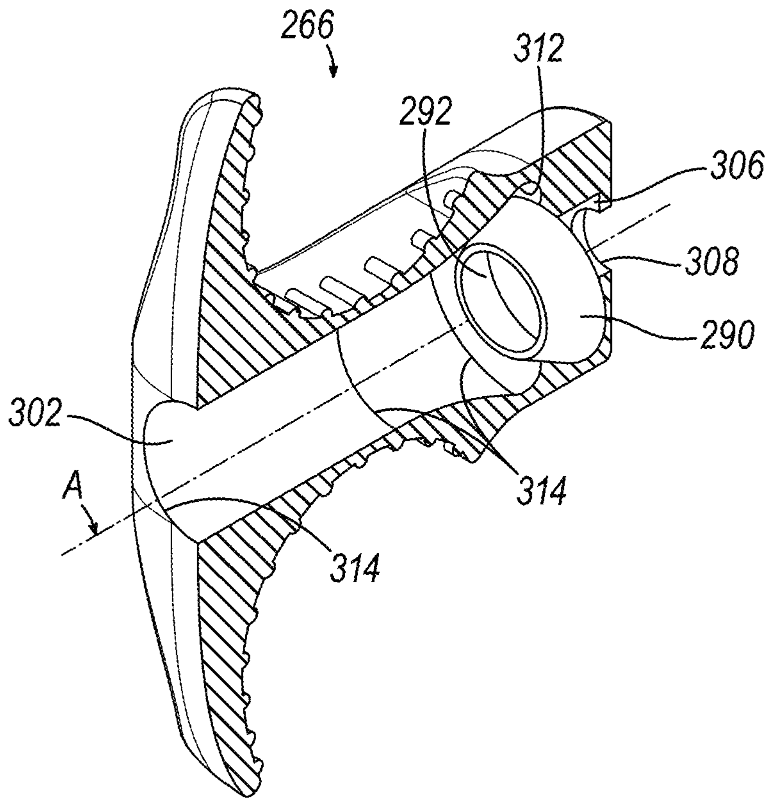
FIG. 7 depicts a partial perspective cross-sectional view of a handle, with the cross-section taken along line 7-7 of FIG. 5.

FIG. 7 shows a handle (266) including a first bore (302), a conical ring (290), a spring holding cavity (292) and a second bore (308). First bore (302) extends distally along longitudinal axis (A) from a proximal end of handle (266) to conical ring (290). At conical ring (290), first bore (302) diverges from longitudinal axis (A) into a first bore cavity (312). Spring holding cavity (292) is located within the conical ring (290). Spring holding cavity (292) extends distally from narrow portion of conical ring (290) to a proximal face (306) of second bore (308). Spring holding cavity (292) is configured to retain a spring (294) (see FIG. 8). Second bore (308) is distally located from spring holding cavity (292). Second bore (308) extends from proximal face (306) to distal end of handle (266). Second bore (308) has a smaller diameter than spring holding cavity (292).

Conical ring (290) has a ramp that includes a wide portion and a narrow portion. Narrow portion is proximally located relative to wide portion. Spring holding cavity (292) is located within conical ring (290). Conical ring (290) is configured to engage angular surface (278) (see FIG. 6) at the narrow portion and expand the distal end of arms (274) as angular surface (278) (see FIG. 6) rides along conical ring (290) to the wide portion.

First bore (302) and first bore cavity (312) have a plurality of interior bands (314). Interior bands (314) can have a variety of geometries. Generally, Interior bands (314) have any geometry complementary to the geometry of the exterior bands (298). Interior bands (314) can be passive grooves or protrusions. Interior bands (314) can have an arcuate shape, a triangular shape, or a rectangular shape. Interior bands (314) are located on an interior surface of first bore (302) and an interior surface of first bore cavity (312). Interior bands (314) are longitudinally spaced to give the operator tactile feedback at different stages of deployment. These stages of deployment can be but are not limited to an undeployed stage (see FIG. 8A), a partially deployed stage (see FIG. 8B), and a deployed stage (see FIGS. 8C and 8D). Interior bands (314) are configured to engage exterior bands (298) (see FIG. 6) with enough resistance to give the operator tactile feedback, but not enough resistance to materially inhibit movement of plunger (270) and push rod assembly (268).

Figure 8A:
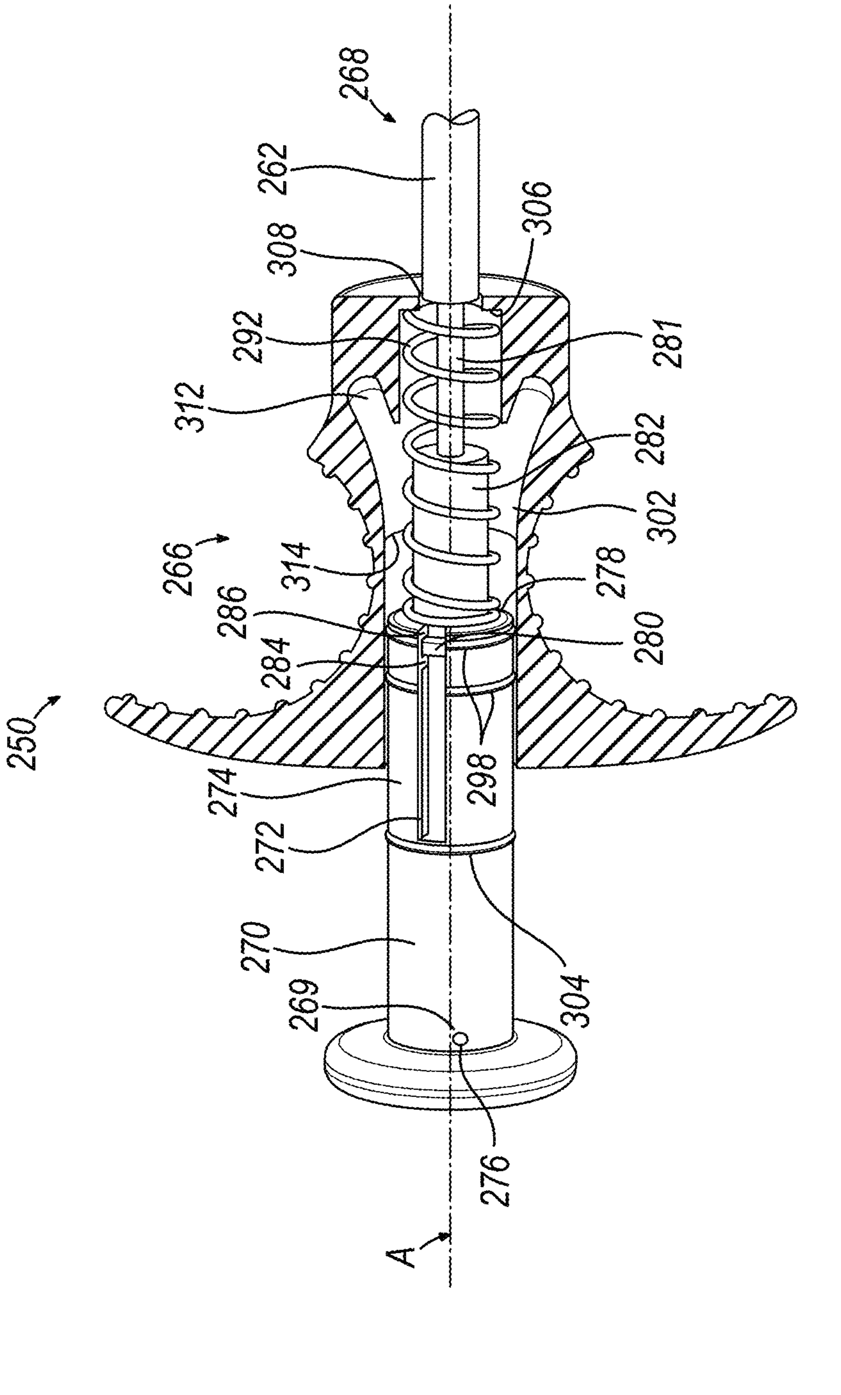
FIG. 8A depicts a partial side cross-sectional view of the marker delivery device of FIG. 5 with the cross-section taken along line 7-7 with the plunger and push rod assembly in an undeployed state.

FIG. 8A shows marker delivery device (250) with push rod assembly (268) in an undeployed state. In the undeployed state, plunger (270) is removably coupled to push rod assembly (268). Arms (274) are in unbiased state with each arm (274) having a respective dog (296) engaging annular ring (280). One or more exterior bands (298) can engage one or more interior bands (314) to resist longitudinal movement of plunger (270). In the undeployed state, exterior bands (298) and interior bands (314) can resist longitudinal movement to keep the operator from inadvertently pushing plunger (270).

Spring (294) is located within spring holding cavity (292) between annular ring (280) and proximal face (306). Spring (294) depicted in FIG. 8A is a helical compression coil spring. Spring (294) is not limited to being configured as helical compression spring. A tension spring may also be used. However, a variety of other springs or other resilient member features can be used. Spring (294) may be any resilient member such as rubber, foam, or belleville washers. Spring (294) biases push rod assembly (268) proximally. Spring (294) is sized to be located around barrel (282) and within spring holding cavity (292).

Figure 8B:
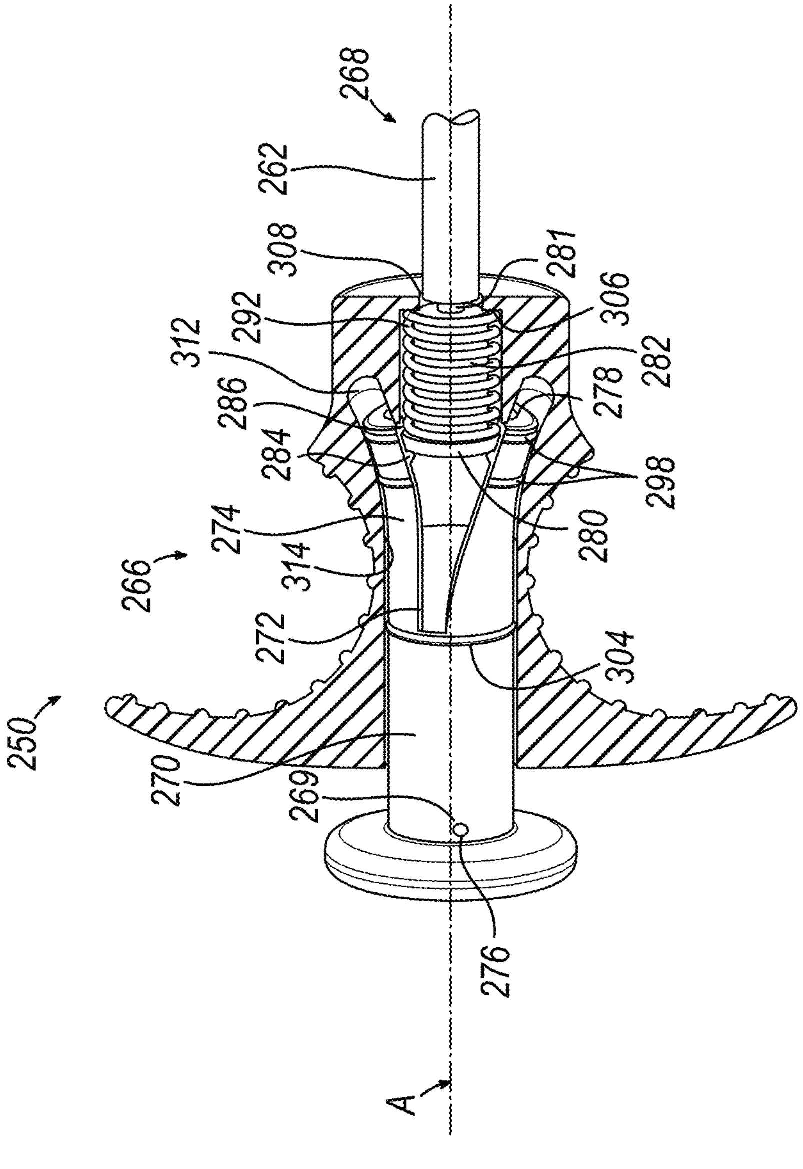
FIG. 8B depicts another partial side cross-sectional view of the marker delivery device of FIG. 5 with the cross-section taken along line 7-7 with the plunger in a partially deployed state and the push rod assembly in a deployed state.

FIG. 8B shows marker delivery device (250) with plunger (270) distally translating push rod assembly (268). To translate plunger (270), an operator can hold grip (266) and push the proximal end of plunger (270) with a thumb or a finger to thereby distally translate plunger (270). Dog (296) remains coupled to annular ring (280), which distally translates push rod assembly (268). Push rod assembly (268) continues to translate distally while plunger (270) is translated until distal end of barrel (282) engages proximal face (306). Barrel (282) is longitudinally sized to allow push rod assembly (268) to translate a specific longitudinal distance before push rod assembly (268) engages proximal face (306). The push rod assembly (268) engages proximal face (306) when angular surface (278) engages narrow portion of conical ring (290). Barrel (282) has a larger diameter than push rod (281). Smaller diameter push rod (281) translates through second bore (308) until barrel (282) stops at proximal face (306). Once barrel (282) engages proximal face (306), push rod assembly (268) stops moving distally, and at this point marker (300) (see FIG. 5) has been deployed through side opening (264) (see FIG. 5). Angular surface (278) of second rib (286) begins to engage conical ring (290). Conical ring (290) begins to deflect arms (274) away from longitudinal axis (A).

Figure 8C:
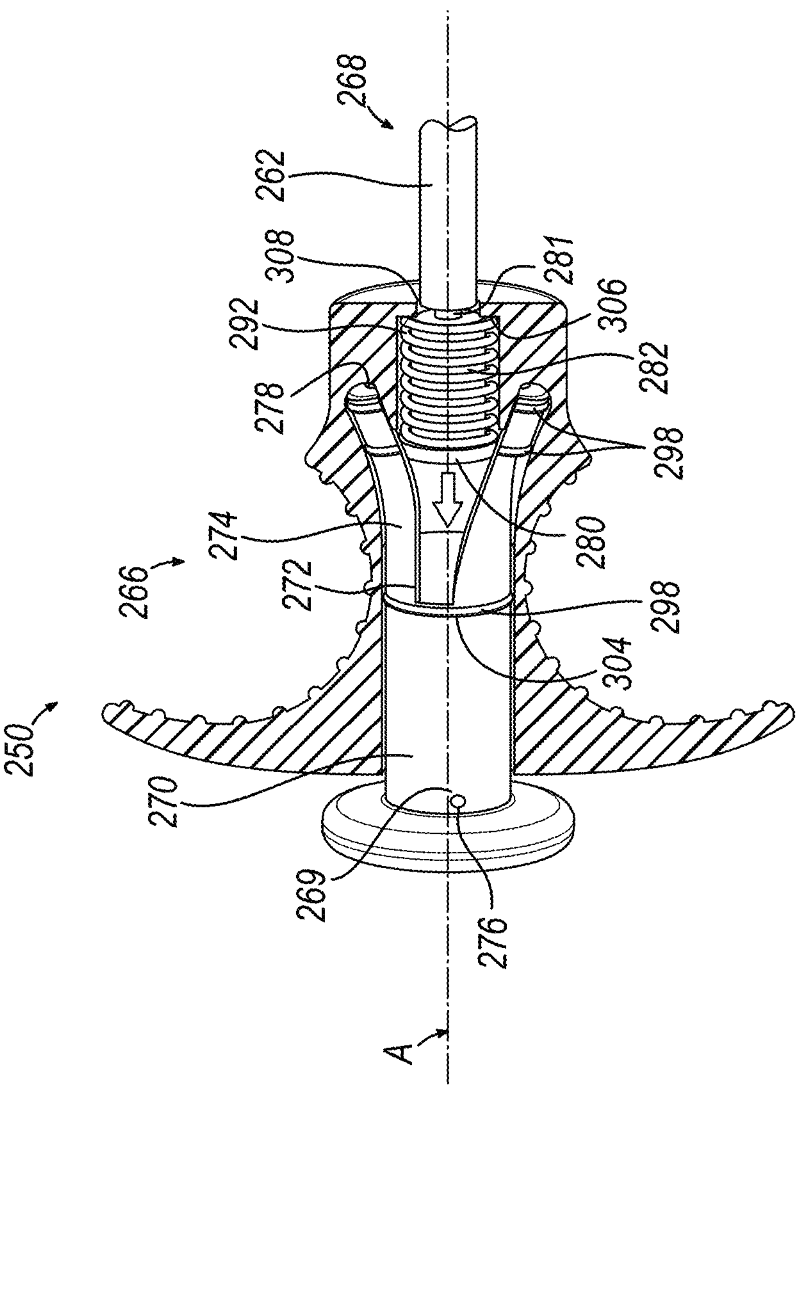
FIG. 8C depicts yet another partial side cross-sectional view of the marker delivery device of FIG. 5 with the cross-section taken along line 7-7 with the plunger in a deployed state and the push rod assembly in a partially retracted state.

FIG. 8C shows marker delivery device (250) with plunger (270) in the deployed state and with plunger (270) distally translated. As plunger (270) is pushed distally, angular surfaces (278) engage narrow portion of conical ring (290) (see FIG. 8B) and angular surfaces (278) ride along narrow portion of conical ring (290) to wide portion of conical ring (290). Arms (274) are transitioned from an unbiased state (see FIG. 8B) to a biased state. Arms (274) are deflected from longitudinal axis (A). Each arm (274) moves radially about arm base (304) away from the longitudinal axis (A). In response to arms (274) being deflected, the interior diameter defined by the first rib (284) of each arm (274) becomes wider than an external diameter of annular ring (280), which allows wider interior diameter of first rib (284) to release annular ring (280). After dog (296) releases annular ring (280), spring (294) begins to proximally translate push rod assembly (268). Prior to dogs (296) being fully translated into first bore cavity (308), interior bands (314) engage exterior bands (298) giving the operator tactile feedback that plunger (270) is close to being fully depressed.

Figure 8D:
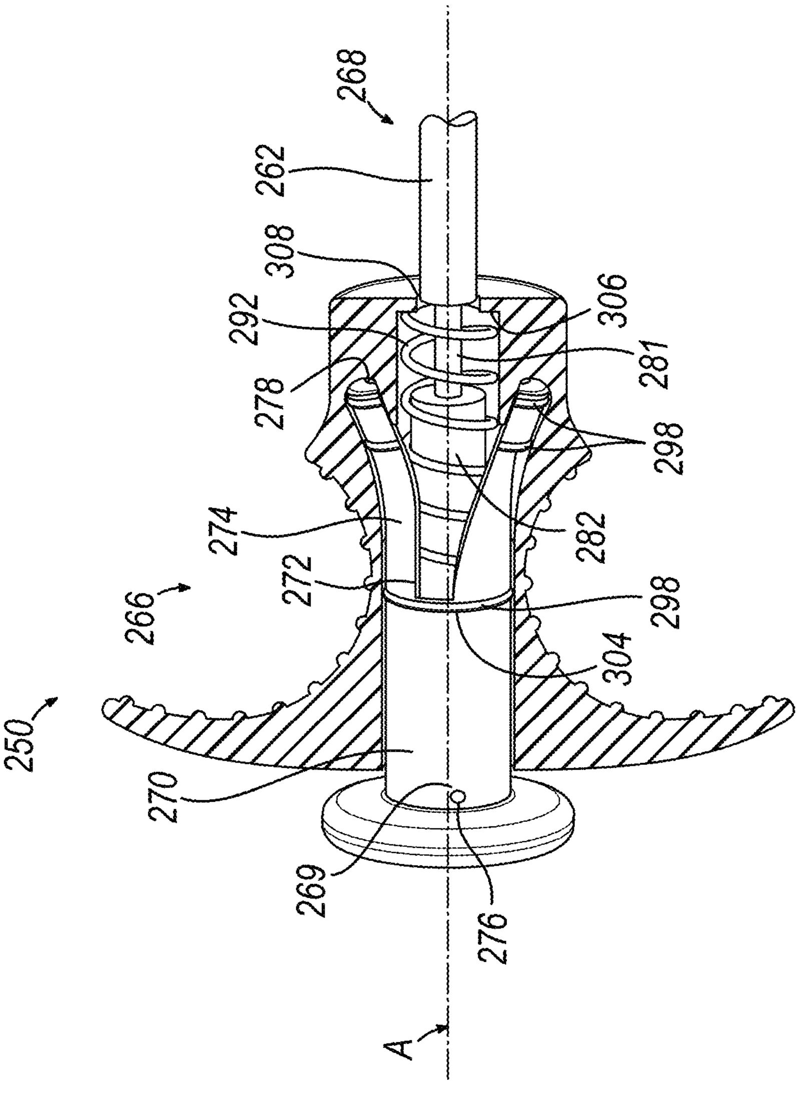
FIG. 8D depicts still another partial side cross-sectional view of the marker delivery device of FIG. 5 with the cross-section taken along line 7-7 with the plunger in deployed state and the push rod assembly in a retracted state.

FIG. 8D shows marker delivery device (250) with plunger (270) fully translated distally, and push rod assembly (268) fully translated proximally. Spring (294) translates push rod assembly (268) proximally until spring (294) is no longer biased to expand, and spring returns to a relaxed state.

Some operators are accustomed to pressing plunger (270), on other marker delivery devices more than once to ensure marker delivery. In other embodiments, handle (266) can have a stop (not shown) to prevent push rod assembly (268) from moving proximally, once spring (294) has retracted push rod assembly (268). This stop (not shown) also keeps spring slightly biased between annular ring (280) (see FIG. 8C) and proximal face (306) of second bore (308). This slight bias on spring (294) can keep spring (294) aligned with longitudinal axis (A). In other embodiments, this stop (not shown) may be located on push rod (281). Stop (not shown) can be located distally in relation to second bore (308) and operatively coupled to push rod (281). This stop (not shown) is configured to inhibit longitudinal movement of push rod (281) through second bore (308) and thereby inhibiting spring (294) from translating push rod assembly (268) proximally. This stop (not shown) can aid the operator in returning plunger (270) and push rod assembly (268) to coupled state (see FIG. 8A) to press plunger (270) more than once. In order to reset plunger (270) and plunger (268) to the undeployed state (see FIG. 8A), the operator translates plunger (270) proximally, while holding handle (266). First rib (284) rides over annular ring (280) (see FIG. 8C), returning annular ring (280) between first rib (284) and second rib (286). In such embodiments, first rib can have a tapered proximal edge (not shown) to aid the operator in retracting plunger (268) within inner bore of handle (266) to retain annular ring (280) between first rib (284) and second rib (286).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such, at a later date by the inventors, or by a successor in interest to the inventors. If any claims are presented in this application or in subsequent filings related to this application that include additional features beyond those referred to below, those additional features shall not be presumed to have been added for any reason relating to patentability.

Example 1

A marker delivery device comprising: a handle including a first bore disposed within the handle; an elongate cannula including a side opening, wherein the elongate cannula extends distally from the handle along a longitudinal axis; a push rod assembly including a mating feature, wherein the push rod assembly is disposed within the first bore and extends distally through the elongate cannula; and a plunger including an engagement feature, wherein the plunger is disposed within the first bore proximal to the push rod assembly, wherein the engagement feature is removably coupled to the mating feature, and the engagement feature is configured to de-couple from the mating feature when the plunger translates the push rod assembly distally.

Example 2

The marker delivery device of Example 1, wherein the handle has a ramped surface located distal in relation to the first bore, and the engagement feature defines an angled surface, wherein the ramped surface is configured to engage the angled surface to de-couple the engagement feature from the mating feature when the plunger is translated distally.

Example 3

The marker delivery device of Example 2, further comprising a spring configured to bias the plunger proximally after the engagement feature de-couples from the mating feature.

Example 4

The marker delivery device of any one or more of Examples 1 through 3, wherein the plunger includes a vent aperture and a hollow, wherein the vent aperture is in a proximal end of the plunger and the vent aperture is in fluid communication with the hollow, wherein the hollow is in fluid communication with the side opening via the cannula.

Example 5

The marker delivery device of Examples 2 through 4, wherein the engagement feature has a first arm biased at an arm base, wherein the first arm is configured to radially deflect at an arm base away from the longitudinal axis when the first arm engages the ramped surface.

Example 6

The marker delivery device of Example 5, wherein the first arm has a first rib configured to engage the mating feature.

Example 7

The marker delivery device of Example 6, wherein the first arm has a plurality of ribs configured to engage the mating feature.

Example 8

The marker delivery device of any one or more of Examples 1 through 7, wherein the mating feature defines a first annular ring.

Example 9

The marker delivery device of any one or more of Examples 1 through 8, wherein the mating feature defines a plurality of annular rings.

Example 10

The marker delivery device of any one or more of Examples 3 through 9, wherein the ramped surface has a spring bore disposed within the ramped surface, wherein the spring bore is configured to retain the spring.

Example 11

The marker delivery device of Example 10, wherein the handle has a second bore distally located from the spring bore and a proximal face located between the spring bore and the second bore, wherein the push rod assembly further includes a barrel and a push rod, wherein the barrel is configured to engage the distal face.

Example 12

The marker delivery device of Example 11, wherein the barrel is configured to stop the longitudinal movement of plunger when the barrel engages the proximal face when the angled surface engages the ramped surface.

Example 13

The marker delivery device of any one or more of Examples 1 through 12, wherein the handle has a plurality of internal surface effects disposed transverse to the longitudinal axis on an interior surface of the first bore, and the plunger has a plurality of external surface effects displaced longitudinally along an exterior surface of the plunger, wherein the external surface effects are configured to engage the internal surface effect to give an operator tactile feedback when the plunger is located at predetermined longitudinal position.

Example 14

The marker delivery device of Example 13, wherein the internal surface effect is a raised portion and the external surface effect is a recessed portion.

Example 15

The marker delivery device of Example 13, wherein the internal surface effect is a recessed portion and the external surface effect is a raised portion.

Example 16

The marker delivery device of any one or more of Examples 13 through 15, wherein the internal surface effect has a triangular shape, a rectangular shape, or an arcuate shape.

Example 17

The marker delivery device of any one of the above Examples 13 through 16, wherein the external surface effect is a triangular shape, a rectangular shape, or an arcuate shape.

Example 18

The marker delivery device of Example 13, wherein the internal surface effect and the external surface effect are configured to engage each other when the plunger is in a most proximal position.

Example 19

The marker delivery device of Example 13, wherein the internal surface effect and the external surface effect are configured to engage each other prior to the engagement feature releasing the mating feature.

Example 20

The marker delivery device of Example 13, wherein the internal surface effect and the external surface effect are configured to engage each other when the plunger is in a most distal position.

Example 21

A marker delivery device comprising: a handle including a conical ring, a first bore, a spring bore, and a second bore, wherein the first bore extends from a proximal end of the handle to the spring bore, wherein the spring bore is disposed within the conical ring and the spring bore extends distally from the first bore to the second bore, and the second bore extends distally from the spring bore to the distal end of handle; an elongate cannula including a side opening, wherein the elongate cannula extends distally from the handle along a longitudinal axis; a push rod including a mating feature, wherein the push rod assembly is disposed within the first bore; and a plunger including an engagement feature, wherein the plunger is disposed within the first bore proximally located in relation to the push rod assembly, wherein the engagement feature removably couples to the mating feature, wherein the engagement feature is configured to de-couple from the mating feature when the engagement feature engages the conical ring.

Example 22

The marker delivery device of Example 21, further comprising a holding feature operatively connected to the push rod distally located relative to the second bore, wherein the holding feature is configured to retain the push rod from being translated proximally once the spring has translated plunger.

Example 23

A marker delivery device comprising: a handle including a first bore, and a conical ring; an elongate cannula including a side opening, wherein the elongate cannula extends distally from the handle along a longitudinal axis; a push rod assembly including an annular ring, wherein the push rod assembly is slidably disposed within the first bore and extends distally through the elongate cannula; and a plunger includes a first arm having a first dog, wherein the plunger is slidably disposed within the first bore and is proximally located in relation to the push rod assembly, wherein the first dog is removably coupled to the annular ring when the delivery device is in a coupled state, wherein the conical ring is configured to deflect the first arm away from the longitudinal axis when the plunger is translated distally to thereby transition the delivery device to an uncoupled state; and a spring configured to bias the plunger proximally when the delivery device is in the uncoupled state.

Example 24

The marker delivery device of Example 23, wherein a barrel is longitudinally sized to engage a proximal face of the second bore and the angled surface of the dog engages the conical ring.

Example 25

The marker delivery device of Example 24, further comprising a spring retainer bore configured to set a push rod assembly stroke and the spring retainer bore has a diameter sized to retain the spring between the annular ring, and a proximal face of the spring retainer bore and the annular ring.

Example 26

A method of deploying a marker using a marker delivery device, the method comprising: pushing a plunger to move a marker through a side opening of an elongate cannula; disengaging the plunger from a push rod assembly; and retracting the push rod assembly with a spring relative to the plunger.

Example 27

The method of Example 26, further comprising engaging an angled surface on an arm of the plunger against a ramped surface on the interior of a handle; displacing the arms away from a longitudinal axis; and releasing the plunger within a hollow of the plunger.

Example 28

The method of Example 27, further comprising venting air through the elongate cannula to the hollow of the plunger, and further venting through a vent aperture in the plunger when the marker is deployed.

Example 29

The method of Example 28, further comprising retracting the push rod assembly with a spring while the plunger remains distal.

Example 30

The method of Example 29, further comprising retracting the plunger proximally; and coupling the plunger with the push rod assembly.

Example 31

The method of Example 30, further comprising inhibiting the push rod assembly from translating proximally once the spring has retracted the push rod assembly with a stop.

V. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A marker delivery device, comprising:
(a) a handle including a first bore disposed within a portion of the handle;
(b) an elongate cannula extending distally from the handle along a longitudinal axis, the elongate cannula being configured to be inserted into a patient;
(c) a push rod assembly including a mating feature, a portion of the push rod assembly being disposed within the first bore and extending distally through the elongate cannula; and
(d) a plunger including an engagement feature, a portion of the plunger being disposed within the first bore proximally of the push rod assembly, the engagement feature being removably coupled to the mating feature, and the engagement feature being configured to de-couple from the mating feature when the plunger translates the push rod assembly distally.

2. The marker delivery device of claim 1, the handle including a ramped surface located distally in relation to the first bore, the engagement feature defining an angled surface, the ramped surface being configured to engage the angled surface to de-couple the engagement feature from the mating feature when the plunger is translated distally.

3. The marker delivery device of claim 2, further comprising a spring configured to bias the plunger proximally after the engagement feature de-couples from the mating feature.

4. The marker delivery device of claim 3, the ramped surface including a spring bore disposed within a portion of the ramped surface, the spring bore being configured to retain the spring.

5. The marker delivery device of claim 4, the handle including a second bore distally located from the spring bore, and a proximal face located between the spring bore and the second bore, the push rod assembly further including a barrel and a push rod, the barrel being configured to engage the proximal face.

6. The marker delivery device of claim 5, the barrel being configured to stop a longitudinal movement of the plunger when the barrel engages the proximal face when the angled surface engages the ramped surface.

7. The marker delivery device of claim 2, the engagement feature including a first arm biased at an arm base, the first arm being configured to radially deflect at the arm base away from the longitudinal axis when the first arm engages the ramped surface.

8. The marker delivery device of claim 7, the first arm including a first rib configured to engage the mating feature.

9. The marker delivery device of claim 8, the first arm having a plurality of ribs configured to engage the mating feature.

10. The marker delivery device of claim 1, the plunger including a vent aperture and a hollow portion, the vent aperture being in a proximal end of the plunger, the vent aperture being in fluid communication with the hollow portion, the hollow portion being in fluid communication with an opening of the cannula.

11. The marker delivery device of claim 1, the mating feature defining a first annular ring.

12. The marker delivery device of claim 1, the mating feature defining a plurality of annular rings.

13. The marker delivery device of claim 1, the handle including a plurality of internal surface effects disposed transverse to the longitudinal axis on an interior surface of the first bore, the plunger including a plurality of external surface effects displaced longitudinally along an exterior surface of the plunger, the external surface effects being configured to engage the internal surface effect to give an operator tactile feedback when the plunger is located at predetermined longitudinal position.

14. The marker delivery device of claim 13, the internal surface effect being a raised portion and the external surface effect being a recessed portion.

15. The marker delivery device of claim 13, the internal surface effect being a recessed portion and the external surface effect being a raised portion.

16. A marker delivery device, comprising:
(a) a handle including a conical ring, a first bore, a spring bore, and a second bore, the first bore extending from a proximal end of the handle to the spring bore, the spring bore being disposed within the conical ring and the spring bore extending distally from the first bore to the second bore, the second bore extending distally from the spring bore to the distal end of handle;
(b) an elongate cannula including a side opening, the elongate cannula extending distally from the handle along a longitudinal axis;
(c) a push rod including a mating feature, a portion of the push rod being disposed within the first bore; and
(d) a plunger including an engagement feature, the plunger being disposed within the first bore, the plunger being disposed proximally of the push rod, the engagement feature being removably coupled to the mating feature, the engagement feature being configured to de-couple from the mating feature when the engagement feature engages the conical ring.

17. The marker delivery device of claim 16, further comprising a holding feature operatively connected to the push rod distally located relative to the second bore, the holding feature being configured to retain the push rod from being translated proximally once the spring has translated plunger.

18. A marker delivery device, comprising:
(a) a handle including a first bore, and a conical ring;
(b) an elongate cannula including a side opening, the elongate cannula extending distally from the handle along a longitudinal axis;
(c) a push rod assembly including an annular ring, the push rod assembly being slidably disposed within the first bore, a portion of the push rod assembly extending distally through the elongate cannula;
(d) a plunger including a first arm having a first dog, the plunger being slidably disposed within the first bore, the plunger being disposed proximally of the push rod assembly, the first dog being removably coupled to the annular ring when the marker delivery device is in a coupled state, the conical ring being configured to deflect the first arm away from the longitudinal axis when the plunger is translated distally to thereby transition the delivery device to an uncoupled state; and
(e) a spring configured to bias the plunger proximally when the marker delivery device is in the uncoupled state.

19. The marker delivery device of claim 18, a barrel being longitudinally sized to engage a proximal face of a second bore, the second bore being distal to the first bore, an angled surface of the first dog being configured to engage the conical ring.

20. The marker delivery device of claim 19, further comprising a spring retainer bore configured to set a push rod assembly stroke, the spring retainer bore having a diameter sized to retain the spring between the annular ring, a proximal face of the spring retainer bore, and the annular ring.

* * * * *